United States Patent
Dove et al.

(10) Patent No.: US 8,211,073 B2
(45) Date of Patent: Jul. 3, 2012

(54) OSTOMY FACEPLATE HAVING MOLDABLE ADHESIVE WAFER WITH DIMINISHING SURFACE UNDULATIONS

(75) Inventors: Michael W. Dove, Gurnee, IL (US); Jeffrey E. Block, Mundelein, IL (US)

(73) Assignee: Hollister Incorporated, Libertyville, IL (US)

( * ) Notice: Subject to any disclaimer, the term of this patent is extended or adjusted under 35 U.S.C. 154(b) by 454 days.

(21) Appl. No.: 12/575,134

(22) Filed: Oct. 7, 2009

(65) Prior Publication Data

US 2010/0324511 A1   Dec. 23, 2010

Related U.S. Application Data

(60) Provisional application No. 61/187,824, filed on Jun. 17, 2009.

(51) Int. Cl.
*A61F 5/44* (2006.01)
(52) U.S. Cl. ........ 604/342; 604/332; 604/336; 604/337; 604/338; 604/339; 604/341; 604/343; 604/344
(58) Field of Classification Search .................. 604/332, 604/336, 337, 338, 339, 341, 342, 343, 344
See application file for complete search history.

(56) References Cited

U.S. PATENT DOCUMENTS

| | | | | |
|---|---|---|---|---|
| 3,339,546 A | * | 9/1967 | Chen | 602/56 |
| 3,457,919 A | * | 7/1969 | Harbard | 602/55 |
| 3,495,592 A | * | 2/1970 | Shepard | 604/336 |
| 3,683,918 A | | 8/1972 | Pizzella | |
| 3,799,166 A | * | 3/1974 | Marsan | 604/336 |
| 3,885,559 A | * | 5/1975 | Economou | 602/55 |
| 3,898,990 A | * | 8/1975 | Nolan | 604/336 |
| 3,941,133 A | * | 3/1976 | Chen | 604/336 |

(Continued)

FOREIGN PATENT DOCUMENTS

AU   581419   2/1989

(Continued)

OTHER PUBLICATIONS

International Search Report and Written Opinion for Application No. PCT/US2010/038969, dated Aug. 24, 2010.

*Primary Examiner* — Tatyana Zalukaeva
*Assistant Examiner* — Ginger T Chapman
(74) *Attorney, Agent, or Firm* — Marshall, Gerstein & Borun LLP

(57) ABSTRACT

An ostomy faceplate and its method of application are disclosed in which the faceplate comprises an annular adhesive wafer of soft, moisture-absorbent, memory-free, essentially non-elastic and finger-moldable adhesive skin barrier material, the wafer's distal surface having an outer zone terminating at the outer periphery of the wafer and an inner zone extending inwardly from the inner limits of the outer zone to a stoma-receiving opening at the inner periphery of the wafer. The faceplate also includes a flexible backing layer covering the outer zone and a removable cover member having a smooth surface releasably covering the proximal bodyside surface of the wafer. The distal surface of the inner zone has undulations defined by a plurality of concentric ridges and valleys with the ridges progressively diminishing in thickness, when measured by the distance between the distal and proximal surfaces at each ridge, as the series progresses inwardly from the maximum thickness of the wafer towards the stoma-receiving opening. The method of application includes both a preliminary molding step and a secondary molding step.

24 Claims, 2 Drawing Sheets

U.S. PATENT DOCUMENTS

| | | | |
|---|---|---|---|
| 4,153,055 A | 5/1979 | Etes | |
| 4,192,785 A * | 3/1980 | Chen et al. | 523/118 |
| 4,204,540 A * | 5/1980 | Cilento et al. | 604/336 |
| 4,231,369 A * | 11/1980 | Sorensen et al. | 604/336 |
| 4,252,120 A * | 2/1981 | Carpenter | 604/336 |
| 4,551,490 A * | 11/1985 | Doyle et al. | 524/22 |
| 4,578,065 A * | 3/1986 | Habib | 604/336 |
| 4,701,169 A | 10/1987 | Steer | |
| 4,723,952 A * | 2/1988 | Esposito | 604/338 |
| 4,768,503 A * | 9/1988 | Highgate et al. | 602/52 |
| 4,808,173 A | 2/1989 | Kay | |
| 4,826,495 A | 5/1989 | Petersen | |
| 4,867,748 A * | 9/1989 | Samuelsen | 604/336 |
| 4,990,144 A * | 2/1991 | Blott | 604/304 |
| 5,000,172 A * | 3/1991 | Ward | 602/52 |
| 5,015,244 A | 5/1991 | Cross | |
| 5,051,259 A * | 9/1991 | Olsen et al. | 424/443 |
| 5,059,189 A * | 10/1991 | Cilento et al. | 604/307 |
| 5,074,852 A | 12/1991 | Castellana et al. | |
| 5,133,821 A * | 7/1992 | Jensen | 156/245 |
| 5,160,330 A | 11/1992 | Cross | |
| 5,185,008 A * | 2/1993 | Lavender | 604/338 |
| 5,346,482 A | 9/1994 | Metz et al. | |
| 5,356,372 A * | 10/1994 | Donovan et al. | 602/58 |
| 5,386,835 A * | 2/1995 | Elphick et al. | 128/846 |
| 5,429,626 A | 7/1995 | Fenton | |
| 5,486,158 A * | 1/1996 | Samuelsen | 602/46 |
| 5,492,943 A * | 2/1996 | Stempel | 523/111 |
| 5,496,296 A * | 3/1996 | Holmberg | 604/336 |
| 5,571,080 A * | 11/1996 | Jensen | 602/56 |
| 5,704,905 A * | 1/1998 | Jensen et al. | 602/58 |
| 5,714,225 A * | 2/1998 | Hansen et al. | 428/114 |
| 5,722,965 A | 3/1998 | Kuczynski | |
| 5,730,735 A * | 3/1998 | Holmberg et al. | 604/338 |
| 5,730,736 A | 3/1998 | Sawers et al. | |
| 5,800,415 A | 9/1998 | Olsen | |
| 5,811,116 A * | 9/1998 | Gilman et al. | 424/443 |
| 5,827,213 A * | 10/1998 | Jensen | 602/62 |
| 5,834,009 A * | 11/1998 | Sawers et al. | 424/443 |
| 6,068,852 A * | 5/2000 | Shah | 424/443 |
| 6,106,507 A * | 8/2000 | Botten et al. | 604/338 |
| 6,206,864 B1 * | 3/2001 | Kavanagh et al. | 604/332 |
| 6,297,423 B1 * | 10/2001 | Schoenfeldt et al. | 602/58 |
| 6,312,415 B1 | 11/2001 | Nielsen et al. | |
| 6,332,879 B1 * | 12/2001 | Nielsen et al. | 604/344 |
| 6,509,391 B2 * | 1/2003 | Gothjaelpsen et al. | 523/111 |
| 6,520,943 B1 | 2/2003 | Wagner | |
| 6,524,699 B1 * | 2/2003 | Himmelsbach et al. | 428/343 |
| 6,589,222 B1 * | 7/2003 | Olsen | 604/336 |
| 6,602,232 B1 | 8/2003 | Keyes | |
| 6,652,496 B2 | 11/2003 | Bateman | |
| 6,685,683 B1 * | 2/2004 | Clok et al. | 604/344 |
| 6,740,067 B2 * | 5/2004 | Leise et al. | 604/332 |
| 6,764,474 B2 * | 7/2004 | Nielsen et al. | 604/344 |
| 6,830,565 B2 * | 12/2004 | Cisko, Jr. | 604/336 |
| 6,840,924 B2 | 1/2005 | Buglino et al. | |
| 6,919,492 B2 * | 7/2005 | Bark et al. | 602/56 |
| 7,172,581 B2 | 2/2007 | Ciok et al. | |
| 7,192,420 B2 | 3/2007 | Whiteford | |
| 7,347,844 B2 | 3/2008 | Cline et al. | |
| 7,507,870 B2 * | 3/2009 | Nielsen et al. | 602/58 |
| 7,586,019 B2 * | 9/2009 | Oelund et al. | 602/55 |
| 7,619,130 B2 * | 11/2009 | Nielsen et al. | 602/58 |
| 7,767,291 B2 * | 8/2010 | Taylor | 428/297.4 |
| 7,777,092 B2 * | 8/2010 | Lykke et al. | 602/55 |
| 7,846,144 B2 * | 12/2010 | Ciok et al. | 604/344 |
| 7,862,878 B2 | 1/2011 | Stroebech et al. | 428/137 |
| 7,875,761 B2 * | 1/2011 | Budig et al. | 602/42 |
| 7,902,420 B2 * | 3/2011 | Kase | 602/55 |
| 8,080,703 B2 * | 12/2011 | Marcussen | 602/55 |
| 2001/0020156 A1 | 9/2001 | Whiteside | |
| 2002/0128580 A1 * | 9/2002 | Carlson et al. | 602/54 |
| 2003/0004477 A1 | 1/2003 | Nielsen et al. | |
| 2003/0093042 A1 * | 5/2003 | Leisner et al. | 604/337 |
| 2004/0102744 A1 * | 5/2004 | Fattman | 604/344 |
| 2004/0106908 A1 * | 6/2004 | Leise et al. | 604/332 |
| 2005/0054997 A1 * | 3/2005 | Buglino et al. | 604/332 |
| 2006/0184145 A1 | 8/2006 | Ciok et al. | |
| 2007/0027434 A1 | 2/2007 | Pedersen et al. | |
| 2007/0078418 A1 * | 4/2007 | May et al. | 604/336 |
| 2007/0154510 A1 * | 7/2007 | Wilcher et al. | 424/422 |
| 2007/0185464 A1 * | 8/2007 | Fattman et al. | 604/336 |
| 2007/0219287 A1 * | 9/2007 | Taylor | 523/111 |
| 2008/0119804 A1 | 5/2008 | Cline et al. | |
| 2009/0148661 A1 | 6/2009 | Stroebech et al. | |
| 2010/0286640 A1 * | 11/2010 | Nordby et al. | 604/336 |

FOREIGN PATENT DOCUMENTS

| | | | |
|---|---|---|---|
| AU | 705091 | | 5/1999 |
| AU | 716253 | | 2/2000 |
| AU | 721675 | | 7/2000 |
| AU | 726169 | | 11/2000 |
| AU | 760036 | | 5/2003 |
| BR | 9809692 | | 7/2000 |
| CA | 1264134 | | 1/1990 |
| CA | 2204614 | | 12/1996 |
| CA | 2198515 | | 8/1997 |
| CA | 2309729 | | 6/1999 |
| CN | 1233945 | | 11/1999 |
| DK | 608184 | | 6/1985 |
| DK | 422386 | | 3/1988 |
| DK | 83391 | | 5/1991 |
| DK | 607/95 | | 11/1996 |
| DK | 173497 | | 4/2007 |
| EP | 0146367 | | 6/1985 |
| EP | 0259184 | | 3/1988 |
| EP | 0276042 | | 7/1988 |
| EP | 0276043 | | 7/1988 |
| EP | 0276898 | | 8/1988 |
| EP | 0413250 | | 2/1991 |
| EP | 0476847 | | 3/1992 |
| EP | 0621042 A1 * | | 4/1994 |
| EP | 0672399 | | 9/1995 |
| EP | 0686381 | | 12/1995 |
| EP | 0793951 | | 9/1997 |
| EP | 0828465 | | 3/1998 |
| EP | 0888760 | | 1/1999 |
| EP | 0938349 | | 9/1999 |
| EP | 0984750 | | 3/2000 |
| EP | 0984751 | | 3/2000 |
| EP | 0985006 | | 3/2000 |
| EP | 0991382 | | 4/2000 |
| EP | 0998247 | | 5/2000 |
| EP | 1033952 | | 9/2000 |
| EP | 1115357 | | 7/2001 |
| EP | 1129680 | | 9/2001 |
| EP | 1164983 | | 1/2002 |
| EP | 1195152 | | 4/2002 |
| EP | 1348411 | | 10/2003 |
| EP | 1348412 | | 10/2003 |
| EP | 1378219 | | 1/2004 |
| EP | 1429696 | | 6/2004 |
| EP | 1477145 | | 11/2004 |
| EP | 1527789 A1 * | | 5/2005 |
| EP | 1585467 | | 10/2005 |
| EP | 1610713 | | 1/2006 |
| EP | 1666008 | | 6/2006 |
| EP | 1815828 | | 8/2007 |
| EP | 2029069 | | 3/2009 |
| GB | 1256866 | | 12/1971 |
| GB | 2226761 | | 7/1990 |
| GB | 2252527 A * | | 8/1992 |
| GB | 2277031 | | 10/1994 |
| GB | 2290974 A * | | 1/1995 |
| GB | 2290974 | | 1/1996 |
| JP | 6070950 | | 3/1994 |
| JP | 9313517 | | 12/1997 |
| JP | 11505754 T | | 5/1999 |
| JP | 2001502570 | | 2/2001 |
| JP | 2001523517 | | 11/2001 |
| NO | 845081 | | 6/1985 |
| NO | 972082 | | 6/1997 |
| NO | 991905 | | 6/1999 |
| NO | 995740 | | 1/2000 |
| NZ | 314147 | | 8/1998 |
| PL | 336960 | | 7/2000 |
| WO | WO 98/17212 | * | 4/1998 |

| WO | WO-98/53771 A1 | 12/1998 |
| WO | WO-99/26565 | 6/1999 |
| WO | WO 99/36017 * | 7/1999 |
| WO | WO-01/85074 | 11/2001 |
| WO | WO-2006/038025 | 4/2006 |
| WO | WO-2008/124717 | 10/2008 |
| ZA | 9701614 | 8/1998 |

* cited by examiner

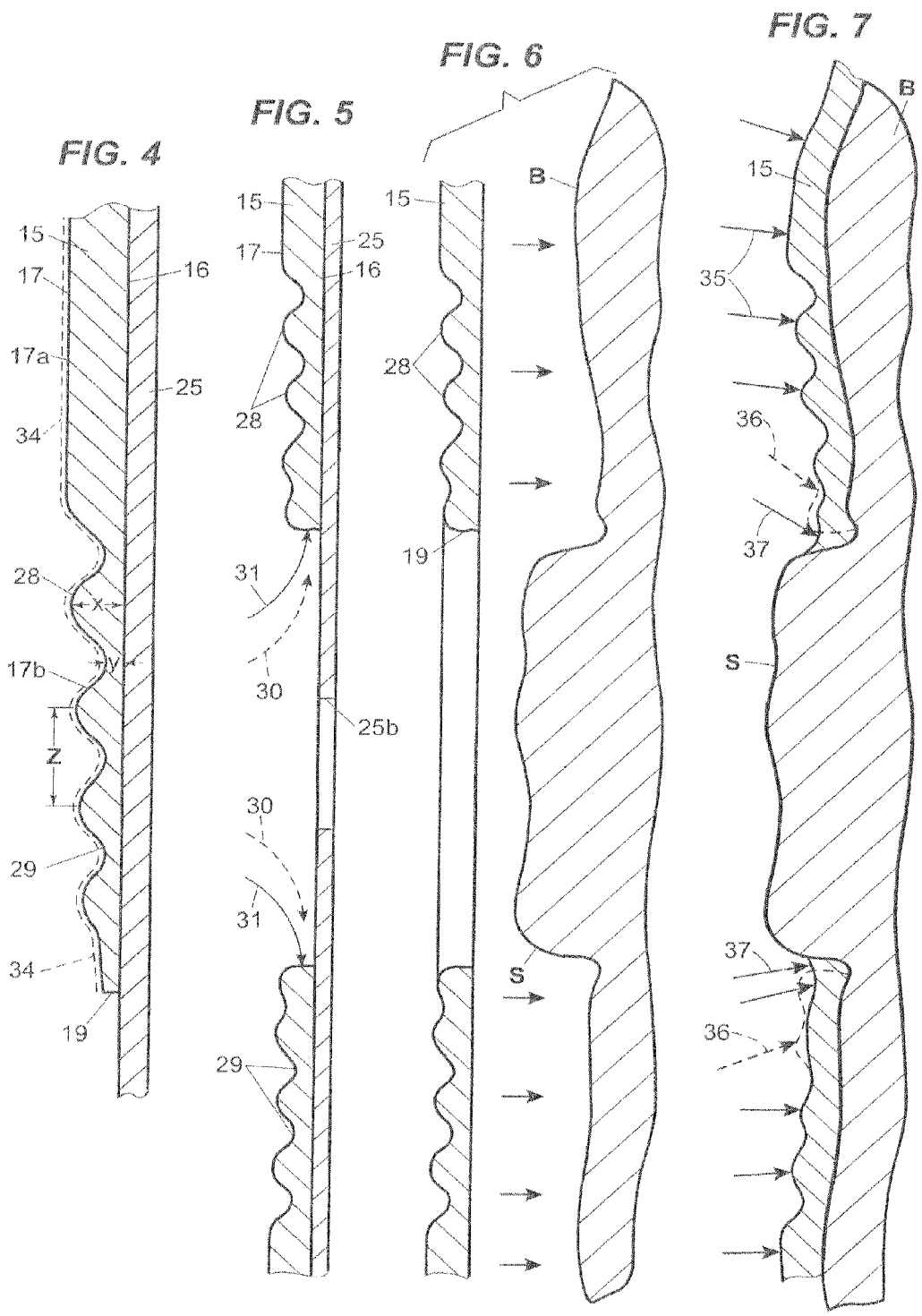

OSTOMY FACEPLATE HAVING MOLDABLE ADHESIVE WAFER WITH DIMINISHING SURFACE UNDULATIONS

This disclosure relates to body waste collection appliances and, more particularly, ostomy appliances in which a moldable adhesive is used to seal the faceplate of the appliance to a wearer's body about a stoma.

BACKGROUND

Ostomy appliances of so-called one-piece and two-piece constructions are commonly provided with adhesive faceplates for adhesively securing the appliances to the peristomal skin surfaces of wearers. For example, patent GB 2 290 974 discloses the faceplate of a two-piece appliance having a coupling ring 12 (to which a collection pouch or bag is to be removably coupled), an annular wafer 18 of medical grade adhesive, and a moldable mass 24 of non-memory putty-like adhesive 24, which may be hydrocolloid or hydrogel based, having a central hole therein. The moldable adhesive mass 24 has a consistency allowing it to be manipulated and pressed into position around a stoma with the fingers. An annular patch 22 of microporous adhesive tape or foam backs the wafer, and the bodyside surface of the wafer is covered with a removable release sheet 26.

U.S. Pat. No. 5,496,296 also discloses an ostomy faceplate having plural adhesives, one which contacts peristomal skin surfaces and performs a load-bearing function, and another which is soft, moldable and extrudable. The moldable adhesive surrounds and contacts the stoma and performs a gasketing or sealing function with respect to the stoma. The latter adhesive is capable of being molded by finger pressure into direct contact with the stoma following initial adhesive attachment of the faceplate to the wearer's body. In attaching a two-piece appliance, the molding step would preferably occur before the pouch is coupled to the faceplate, whereas the procedure with a one-piece appliance might require at least part of the molding step to occur by finger pressure applied through the front or distal wall of the pouch after the appliance has been adhered to the body.

Despite their advantages in forming fluid-tight gaskets or seals against a stoma, such putty-like moldable adhesives have been reported as lacking cohesive strength and being subject to cold flow. Thus, the point has been made that the required lack of memory of a moldable adhesive such as disclosed in the aforementioned British patent 2 290 974 results in the disadvantage that the adhesive may creep or flow under ambient conditions or during use. That problem has been addressed by chemically or physically crosslinking one or more of the components of the non-hydrocolloid portion of such an adhesive, but the incorporation of crosslinks then may have the disadvantage of introducing significant elasticity into the adhesive (see published application US 2007/0185464 A1).

In U.S. Pat. No. 6,332,879, elasticity or recoverability is purported to be advantageous in a hydrocolloid adhesive wafer having a sealing member with "balanced" plastic and elastic properties because it allows temporary enlarging of the hole through the wafer, to adapt it for accommodating a stoma, by everting or rolling the rim of the hole upon itself. After having been placed over and around the stoma, the elasticity of the wafer allows it to recover essentially to its original form to fit snugly about the stoma. In one embodiment, the sealing member is provided with grooves encircling a central stoma receiving opening for enlargement of the stoma receiving opening by lateral displacement outwardly of the rim compressing the grooves after which the sealing member, because of its elastic properties, expands to provide a snug fit to the stoma.

In contrast to a hydrocolloid adhesive having balanced plastic and elastic properties, one that may be regarded as being only moldable is essentially devoid of memory and elastic recoverability. While some strain recovering properties may exist, they are too limited to be of significance in affecting the putty-like non-memory characteristics of such a moldable adhesive. Thus, publication WO 2007/076862 discloses a layered adhesive construct designed for skin contact in which the construct has two (or more) layers of hydrocolloid adhesive. Only the first layer is identified as being of a moldable adhesive and, by definition, its Strain Recovery is required to be below 45%, preferably below 35%, when measured as described in the disclosure. By contrast, the hydrocolloid adhesive of the second layer, which is not identified as being moldable, is required to have a Strain Recovery above 55%.

Other patents and publications illustrative of the state of the art are: U.S. Pat. No. 6,840,925; US 2006/0184145; U.S. Pat. No. 6,764,474; GB 2 277 031; WO 2006/038025; U.S. Pat. Nos. 6,652,496; 6,312,415; U.S. Pat. No. 5,074,852; EP 0 888 760; U.S. Pat. No. 6,509,391; EP 0 991,382; US 2005/054997; U.S. Pat. No. 3,683,918; U.S. Pat. No. 7,172,581; U.S. Pat. No. 6,589,222; U.S. Pat. No. 5,147,340; U.S. Pat. No. 3,667,469; WO 2007/076682; EP 1 164 983.

SUMMARY OF THE DISCLOSURE

An important aspect of this invention lies in providing an improved ostomy faceplate and method of use in which an adhesive wafer of hydrocolloid-containing skin barrier material may be molded more effectively than the barrier materials of prior ostomy faceplates into sealing contact with a stoma and skin surfaces surrounding the stoma. The skin barrier material of the adhesive wafer is soft, readily formable with the fingers, and essentially devoid of elastic recovery and memory. In contrast to so-called moldable barrier materials of the prior art, which may have Strain Recovery values approaching 45%, the putty-like skin barrier material of the adhesive wafer of this faceplate has a Strain Recovery well under 25%, preferably under 15%. Because of its relatively low Strain Recovery and also because it is in fact an absorbent pressure-sensitive adhesive having both wet and dry tack that adheres to and seals readily against the skin as well as the stoma, while at the same time having low cold flow and high cohesive strength, it does not exhibit any significant elastic retraction following application to body tissues.

The adhesive wafer of this disclosure has a proximal bodyside surface and an opposite distal surface, with the distal surface having an outer zone terminating at the outer periphery of the adhesive wafer and a concentric inner zone extending inwardly from the outer zone to a stoma-receiving opening at the inner periphery of the adhesive wafer. A flexible backing covers the outer zone of the distal surface of the adhesive wafer and a smooth cover member removably covers the proximal bodyside surface of the adhesive wafer. Of significance is the fact that the inner zone of the distal surface of the adhesive wafer has undulations defined by a series of concentric ridges and valleys with the ridges progressively diminishing in thickness, when measured by the distance between the distal and proximal surfaces at each ridge, as the series progresses radially inwardly from a maximum thickness of the adhesive wafer towards a minimum thickness surrounding the stoma-receiving opening.

The result is an adhesive wafer in which the opening may be easily enlarged and reshaped with the fingers by slidably displacing the skin barrier material upon the smooth surface of the cover member until the opening has the general shape and size of the wearer's stoma. Such enlargement and reshaping is facilitated by the relative thinness of the barrier material in the region of the opening and by the concentric ridges and valleys of diminishing size that may be compressed or gathered in accordion-like fashion about the opening. After the opening has been reshaped and sized by slidable displacement of the barrier material on the cover member, the cover member is removed and the proximal surface of the adhesive wafer is positioned in adhesive sealing engagement with skin surfaces surrounding the stoma. The final steps involve inwardly displacing and molding the barrier material by means of finger pressure into sealing contact with the stoma that extends through the stoma receiving opening of the adhesive wafer and, if the wafer has a tape border, then peeling away the release strip(s) extending over the adhesive coating of the tape and adhesively securing the tape to the wearer's skin.

Other features, advantages and objects of the invention will become apparent from the specification and drawings.

BRIEF DESCRIPTION OF THE DRAWINGS

FIG. 4 is a further enlarged fragmentary sectional view of the moldable adhesive wafer showing its surface undulations of diminishing size.

FIGS. 5, 6 and 7 illustrate successive steps in the method of application of an ostomy faceplate embodying the invention.

DETAILED DESCRIPTION OF PREFERRED EMBODIMENTS

Figure 1:
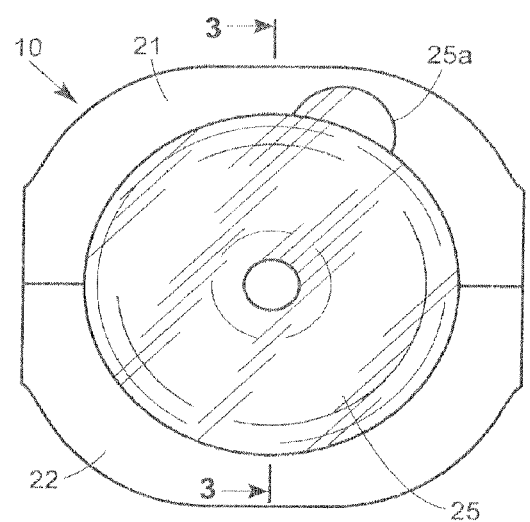
FIG. 1 is an elevational view from the distal side of an ostomy faceplate embodying the invention.
Figure 2:
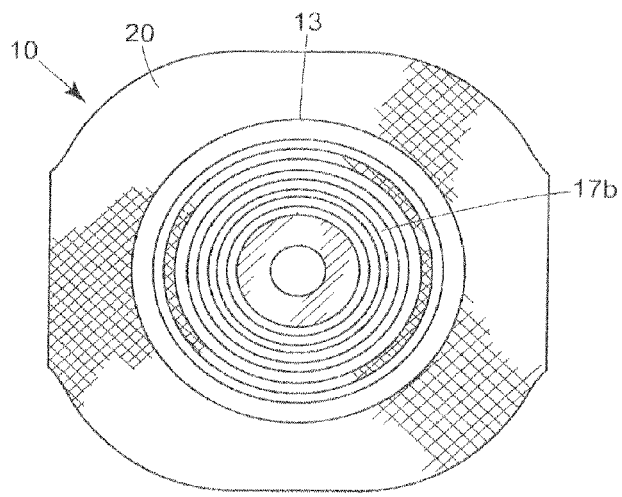
FIG. 2 is an elevational view taken from the proximal side of the faceplate.
Figure 3:
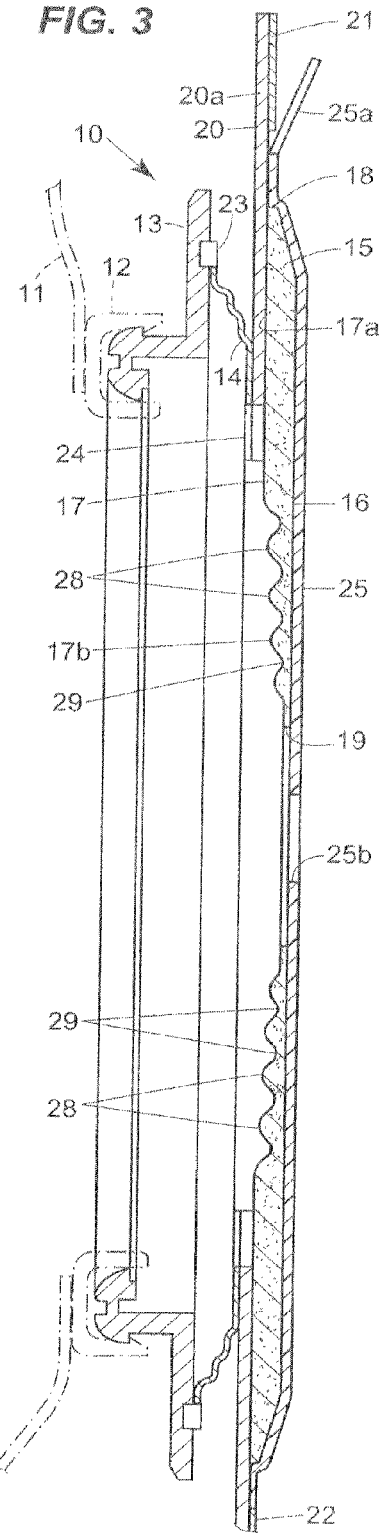
FIG. 3 is an enlarged vertical sectional view taken along line 3-3 of FIG. 1.

Referring to FIGS. 1-3 of the drawings, the numeral 10 generally designates the faceplate of a two-piece ostomy appliance. The other component of the appliance is a conventional pouch 11 with a coupling ring 12 indicated in phantom in FIG. 3. Since the pouch component does not constitute part of this invention, further description of that component is believed unnecessary herein. However, reference may be had to U.S. Pat. No. 5,185,008 for details of the depicted coupling system. It should be understood that instead of the mechanical coupling rings shown, the coupling elements may take the form of rings that adhesively couple together, preferably by an adhesive attachment that also allows intentional separation of the parts when removal and replacement of only the pouch component is desired.

The faceplate 10 comprises a faceplate coupling ring 13, a connecting web 14, and an adhesive wafer 15. The adhesive wafer 15 has a proximal and generally planar bodyside surface 16 and an opposite distal surface 17. As shown most clearly in FIG. 3, the distal surface 17 includes an outer zone 17a terminating at an outer periphery 18 of the adhesive wafer 15 and a concentric inner zone 17b extending radially inwardly from the outer zone 17a to a stoma-receiving opening 19 at the inner periphery of the adhesive wafer 15.

A backing layer 20 covers the outer zone 17a of the distal surface 17 of the adhesive wafer 15. The backing layer 20 may be of thin, flexible, fabric, film or foam; however, it is especially desirable that it be composed of a porous heat-sealable material. Effective results have been obtained using a microporous nonwoven tape of polyolefinic fibers, but other soft breathable or non-breathable thermoplastic materials may be used. The tape may be coated on its proximal surface with a suitable pressure sensitive adhesive, such as a conventional hypoallergenic medical-grade acrylic adhesive, which securely bonds it to the outer zone 17a of the distal surface 17 of the adhesive wafer 15. Of importance is the fact that the tape with its adhesive coating extends outwardly beyond the outer periphery 18 of the adhesive wafer 15, thereby providing a tape border 20a that adhesively contacts the wearer's skin when the faceplate 10 is applied and performs a significant load-bearing function for the appliance and its body waste contents. The tape border 20a also shields the outer periphery 18 of the adhesive wafer 15 against water contact (as when the wearer showers) and protects against contact with objects that might unintentionally peel the faceplate 10 away from the skin when the appliance is worn.

The adhesive coating of the tape border 20a is shown in FIGS. 1 and 3 to be covered by one or more release strips which may take the form of a pair of generally semi-circular release strips 21 and 22 of siliconized paper or other suitable material. Such release strips 21 and 22 may then be peeled away to expose the adhesive for adhering the tape border 20a to the skin in the final stages of securing the faceplate 10 to a wearer.

The connecting web 14 is depicted as being heat-sealed at 23 and 24 to both the faceplate coupling ring 13 and the backing layer 20. It connects the parts together in a way that allows limited independent movement of the faceplate coupling ring 13 and permits a wearer or caregiver to place his/her fingers between the faceplate coupling ring 13 and the backing layer 20 to facilitate attachment of the coupling rings 13 and 12 to each other, thereby creating an arrangement that has been referred to as a "floating flange" construction.

The proximal or bodyside surface 16 of the adhesive wafer 15 is covered by a removable cover member 25 illustrated most clearly in FIGS. 1 and 3. The cover member 25 is generally planar and of circular outline, although it preferably includes an outwardly-projecting finger tab 25a to be gripped by a user when the cover member 25 is to be peeled away to expose the proximal surface 16 of the adhesive wafer 15. Ideally, the cover member 25 should be transparent or translucent. While a clear plastic material such at polyethylene terephthalate has been found suitable, other flexible plastic materials having similar properties may be used. Of particular importance, the forces adhering the cover member 25 to the adhesive wafer 15 should be weak enough to allow a user to slide or shift the barrier material of the adhesive wafer 15 along the distal surface of the cover member 25 during a preliminary molding operation as described in greater detail below. For that purpose, the distal surface of the cover member 25 may be coated with silicone or some other release agent that permits such slipping action during the initial molding step.

The hydrocolloid barrier material of the adhesive wafer 15 must be moldable and notably lacking in elastic properties, in sharp contrast to barriers known in the prior art reported to have balanced plastic and elastic properties. Even when compared with prior hydrocolloid adhesives considered to be moldable, the Strain Recovery of the adhesive of adhesive wafer 15 is far lower. Thus, the adhesive of publication WO 2007/076862 selected for its properties of moldability, is claimed to have a Strain Recovery after deformation that may exceed 40% when tested by a procedure outlined in that publication, whereas the moldable hydrocolloid adhesive of the adhesive wafer 15, measured by a similar test as described in Example 2 below, should have a Strain Recovery value under 25%, preferably under 15%.

The adhesive of the adhesive wafer 15 is most advantageously made in accordance with the teaching of co-owned application US 2007/0219287, published Sep. 20, 2007, the entire disclosure of which is incorporated by reference herein. The adhesive composition comprises a network of entangled fibrillated polymeric fibers having a surface area of at least 4 m$^2$/g, a continuous pressure-sensitive adhesive phase coating such fibers, and a discontinuous phase comprising particles of one or more liquid absorbing and swellable hydrocolloids dispersed throughout that network. The pressure-sensitive adhesive phase may be polyisobutylene (PIB) and the fibrillated fibers may be comprised of a polyolefin such as polyethylene, the latter constituting about 1% to about 5% of the total weight of the composition (hereafter referenced as wt/%). The hydrocolloids may advantageously comprise a mixture of pectin and sodium carboxymethylcellulose that may constitute about 10 to 50 wt/% of the composition. As disclosed in the aforementioned publication, variations in proportions, in the compositions of the components and their molecular weights, and other variations may occur depending on whether a given composition is intended to be used as a moldable skin barrier (of relatively high viscosity) or as a paste (of relatively low viscosity). Thus, a moldable skin barrier for use in this invention might contain medium molecular weight PIB (having an average molecular weight of about 10,000 to 40,000) in the range of 50 to 65 wt/% of the composition and 0 to about 10 wt % of low molecular weight polyisobutylene (having an average molecular weight within the range of about 1,000 to 4,000).

Example 1

An illustrative moldable skin barrier composition for use in this invention may be prepared using 55 wt./% 36,000 molecular weight PIB, 4 wt./% fibrillated polyethylene fiber (surface area of 8 m$^2$/g, fibril length about 0.55 to 0.85 mm, fibril diameter about 15μ), 13.7 wt./% pectin, and 27.3 wt./% sodium CMC. The composition may be prepared using a Brabender Type REE6 mixer at 50° C. The ingredients may be added in the order given above, and after the addition of each ingredient, mixing is allowed to proceed until the mixture is homogeneous. After the final mixing period, the mixture is removed from the mixer and allowed to equilibrate at room conditions.

Example 2

Three sample disks A-C of moldable skin barrier compositions made in accordance with the process set forth in Example 1 were analyzed for Strain Recovery on a TA Instruments AR2000 Rotational Rheometer with the following test parameters:
Gap: 1000 μm;
Test Mode: Viscometry;
Fixture: 25 mm Parallel Plate, MELT;
Temperature: 32° C.

Each sample disk was placed on the rotational rheometer fixture that was preheated to the specified temperature. The upper portion of the fixture was lowered to the specified gap, the sample was trimmed, and the analysis was run.

A shear deformation of 15% and 5% (total 20%) was applied in two steps in order to avoid overshoot in deformation. The overshoot of the deformation did not exceed 22%. The total time of the deformation was less than 90 seconds. The stress was removed and the remaining elastic forces recovered some of the applied deformation. The resulting recovery of the deformation was measured after an elapse of 1000 seconds.

The Strain Recovery is defined as the percentage recovery from large step strain and is calculated as follows:

$$\text{Strain Recovery} = (\gamma - \gamma^{1000})/\gamma$$

where γ is 0.20 and $\gamma^{1000}$ is the shear deformation after 1000 seconds.

| Sample Identification | Percentage Strain Recovery |
| --- | --- |
| Sample A | (0.2-0.1766)/0.2 = 0.1170 = 12% |
| Sample B | (0.2-0.1770)/0.2 = 0.1150 = 12% |
| Sample C | (0.2-0.1653)/0.2 = 0.1735 = 17% |

Sample A had the following composition:
PIB (molecular weight 51,000) 55 wt./%
Polyethylene Fibers 4 wt./%
Pectin 13.7 wt./%
CMC 27.3 wt./%

Sample B was of the same composition specifically referenced as an illustrative composition in Example 1 above.

Sample C had the following composition:
PIB (molecular weight 36,000) 55 wt./%
Liquid PIB (having an average molecular weight within the range of about 1,000 to 4,000) 5 wt./%
Polyethylene Fibers 2 wt./%
Pectin 13 wt./%
CMC 25 wt./%

While the hydrocolloid-containing adhesive compositions with fibrillated polymeric fibers referenced above and disclosed in greater detail in publication US 2007/0219287 are highly regarded for their ease of moldability, low recovery, absence of memory, low cold flow and high cohesive strength, and are therefore believed to be particularly suitable for use in this invention, it is to be understood that other moldable skin barrier compositions might be formulated having at least some of the same properties and might be suitable for the formulation for the adhesive wafer 15.

FIG. 4 illustrates the radial cross-sectional configuration of the adhesive wafer 15. The adhesive wafer 15 is shown to be of maximum thickness, and also of uniform thickness, in outer zone 17a, whereas in inner zone 17b the adhesive wafer 15 progressively diminishes in thickness as a function of radial inward location toward the stoma-receiving opening 19 of the adhesive wafer 15, and also has a distal surface with undulations defined by a series or plurality of concentric ridges 28 and valleys 29 with the ridges 28 progressively diminishing in thickness or amplitude as the series progresses from the outer zone 17a toward the stoma-receiving opening 19. The combination of the undulations and the progressive diminution in the thickness of the ridges 28 in an inward direction has several important effects. The valleys 29 between the ridges 28 promote flexibility of the adhesive wafer 15 and help it adapt to changes in body contour as a wearer moves about. The valleys 29 also serve as compression zones, allowing the ridges 28 to move into closer proximity during an initial molding operation as the stoma-receiving opening is being enlarged and/or reshaped to match the size and shape of the wearer's stoma. During such an initial molding step, forces are applied with the fingers in the directions indicated by arrows 30 and 31 in FIG. 5, slidably displacing the moldable barrier material along the smooth distal surface of the cover member 25 immediately surrounding the stoma-receiving opening 19 to increase the thickness of that barrier material while at the same time avoiding any lifting or rolling back of the relatively thin barrier material about the stoma-receiving opening 19. The fact that the ridges 28 nearest the stoma-receiving opening 19 are of reduced thickness or amplitude compared with those closer to the outer zone 17a is particularly significant because as the barrier material about the opening is slidably displaced upon the cover member 25 to urge together the ridges immediately about the opening, the accumulation of barrier material caused by such action is insufficient to promote a lifting or rolling back of the displaced material. As shown most clearly in FIGS. 5 and 6, enlargement of the stoma-receiving opening 19 is therefore achieved without objectionable lifting, folding or rolling of the barrier material about that opening during the preliminary molding step.

The cover member 25 with its friction-limiting distal surface remains in place throughout the initial molding step since it provided the sliding surface that supports the adhesive wafer 15 as the size and shape of the stoma-receiving opening 19 are being changed. It has been found that some wearers with greater dexterity and experience may be able to reshape the stoma-receiving opening 19 during the initial molding step so that it closely matches the dimensions and shape of their stoma. Others may find it easier to slidably enlarge the opening 19 so that it exceeds the size of their stoma, instead relying on the second molding step (FIG. 7) to reduce the size of the stoma-receiving opening 19 to the stoma's external dimensions.

It will be noted that the cover member 25 has an aperture 25b concentric with but smaller than the stoma-receiving opening 19 of the adhesive wafer 15. Aperture 25b is a starter opening for those wearers who may be accustomed to shaping and increasing the size of a stoma-receiving opening by a cutting operation. In such a case, the aperture 25b and stoma-receiving opening 19 may be cut to size with scissors rather than by the initial finger-molding step described above. However, the fact that the aperture 25b is smaller than the opening 19 in the faceplate as shown also benefits those wearers that prefer to follow the preliminary molding procedure because the exposed distal surface of the cover member immediately about the aperture provides a smooth sliding surface for directing and controlling finger contact with the barrier material at the time the preliminary molding step is commenced.

A series of five ridges 28 and valleys 29 are shown in the drawings, but it is to be understood that the number may be greater or smaller depending largely on the size of the faceplate. Generally, the number of ridges 28 and valleys 29 will range between two and ten. The outermost ridge 28 may have a thickness "x" corresponding to or approximating the maximum thickness of the adhesive wafer 15 along outer zone 17a and its thickness "x" should fall within the range of from about 0.04 to about 0.10 inches. In the valleys 29, the thickness "y" should fall within the range of from about 10% to about 60%, preferably from about 20% to about 40%, of the maximum thickness of the adhesive wafer 15. Successive ridges of the series may be spaced apart at distances "z" measured radially from about 0.05 to about 0.20 inches, preferably from about 0.08 to about 0.15 inches. The thickness of the ridges 28 progressively decreases from the ridge 28 of greatest thickness closest to the outer zone 17a to a thickness of about 0.02 to about 0.06 inches for the ridge 28 closest to opening 19, with the ridge of least thickness being 40% to 80%, preferably 50% to 70%, of the thickness of the ridge 28 of greatest thickness.

The distal surface 17 of the adhesive wafer 15 may be protected by a non-tacky dead-stretch film or coating 34 (represented by a broken line in FIG. 4) that covers the undulating adhesive surface 17b facing the pouch 11 and prevents direct contact between the moldable adhesive of the adhesive wafer 15 and the inside wall of the pouch 11. By "dead-stretch" is meant a film or coating that is highly stretchable (that has a yield point at a low load) but has no appreciable elastic recovery. Such a film should also be isotropic, that is, its mechanical properties should be essentially equivalent in all directions. A film such as Parafilm® M, manufactured by Pechiney Plastic Packaging, Inc., of Chicago, Ill., is a film material suitable for the protective film 34, but other film materials having similar dead-stretch isotropic properties may be used.

The protective film 34 prevents adhesion between the distal wall (not shown) of the pouch 11, exposed through the pouch opening, and the adhesive wafer 15, since such adhesion would have the effect of obstructing the entry of waste material into the pouch 11. The film 34 also protects the moldable adhesive of the adhesive wafer 15 from contacting output from the stoma S and/or contents of the pouch, such as stomal effluent, which might otherwise cause erosion of the moldable adhesive. For the same reason, it is desired that the protective film 34 remains intact on the distal side of the adhesive wafer 15 during and following a molding operation, and that the adhesive wafer 15 not be folded, rolled or otherwise deformed to expose its tacky adhesive material in a distal direction during and following the preliminary molding operation depicted in FIG. 5.

Following removal of the cover member 25 from the proximal surface 16 of the adhesive wafer 15, the proximal surface 26 is brought into contact with the wearer's body B about stoma S as indicated in FIG. 6. The adhesive wafer 15 may be pressed in the direction of arrows 35 into sealing contact with the peristomal skin surfaces followed by finger pressure applied to the adhesive wafer 15's inner peripheral portion (arrows 36 and 37 of FIG. 7) to displace, deform, and mold the barrier material into whatever crevices may exist immediately about the stoma S, thereby sealing the adhesive wafer 15 to the stoma S in a second molding step. The final steps comprise peeling away the release strips 21 and 22 from the adhesive coating of the tape backing layer 20 and adhering the tape border 20a to the skin, followed by attachment of the coupling ring 12 of the pouch component to the mating faceplate coupling ring 13.

The invention claimed is:

1. An ostomy faceplate comprising a generally annular adhesive wafer of soft, moisture-absorbent, finger-moldable, essentially non-elastic skin barrier material;
    said wafer having a proximal bodyside surface and an opposite distal surface;
    said distal surface having an outer zone terminating at an outer periphery of said wafer and a concentric inner zone extending inwardly from said outer zone to a stoma-receiving opening at an inner periphery of said wafer;
    a flexible backing layer covering said outer zone of said distal surface;
    and a removable cover member having a smooth surface releasably covering said proximal bodyside surface of said wafer;
    said distal surface of said inner zone having undulations defined by a series of concentric ridges and valleys with said ridges progressively diminishing in thickness, when measured by the distance between said distal and proximal surfaces at each ridge, as said series progresses inwardly from the maximum thickness of said wafer towards said stoma-receiving opening of said wafer.

2. The ostomy faceplate of claim 1 in which said series comprises 2 to 10 of said ridges.

3. The ostomy faceplate of claim 1 in which said valleys and said ridges of progressively diminishing thickness are covered by a stretchable non-tacky film having substantially dead-stretch isotropic properties.

4. The ostomy faceplate of claim 2 in which the maximum thickness of said wafer is in a range of from about 0.04 to about 0.10 inches.

5. The ostomy faceplate of claim 4 in which the thickness of said wafer at said valleys falls within a range of from about 10% to about 60% of the maximum thickness of said wafer.

6. The ostomy faceplate of claim 5 in which said range is from about 20% to about 40%.

7. The ostomy faceplate of claim 1 in which successive concentric ridges of said series are spaced apart at distances measured radially in a range of from about 0.05 to about 0.20 inches.

8. The ostomy faceplate of claim 7 in which successive ridges are spaced apart at distances measured radially in a range of from about 0.08 to about 0.15 inches.

9. The ostomy faceplate of claim 1 in which said ridges progressively diminish in thickness, when measured by the distance between said distal and proximal surfaces at each ridge, from a thickness in a range of from about 0.04 to about 0.10 inches for the ridge closest to said outer zone to a thickness in a range of from about 0.02 to about 0.06 inches for the ridge nearest said stoma-receiving opening, with the ridge of least thickness being in the range of about 40% to 80% of the thickness of the ridge of greatest thickness.

10. The ostomy faceplate of claim 9 in which said ridge of least thickness is about 50% to 70% of the thickness of said ridge of greatest thickness.

11. The ostomy faceplate of claim 1 in which said adhesive wafer has a composition comprising a network of entangled fibrillated polymeric fibers having a surface area of at least 4 $m^2/g$, a continuous pressure-sensitive adhesive phase coating such fibers, and a discontinuous phase comprising particles of one or more liquid absorbing and swellable hydrocolloids dispersed throughout said network.

12. The ostomy faceplate of claim 11 in which said polymeric fibrillated fibers are comprised of polyethylene and constitute about 1% to about 5% by weight of said composition.

13. The ostomy faceplate of claim 12 in which said continuous phase includes medium molecular weight polyisobutylene having an average molecular weight within the range of about 10,000 to 40,000.

14. The ostomy faceplate of claim 13 in which said hydrocolloids comprise a mixture of pectin and carboxymethylcellulose.

15. The ostomy faceplate of claim 1 in which said flexible backing layer comprises a sheet of porous polymeric fabric, film or foam.

16. The ostomy faceplate of claim 15 in which said backing layer comprises a tape that extends outwardly beyond the outer periphery of said wafer, and has a pressure sensitive adhesive coating on the proximal surface thereof, to provide an adhesive tape border surrounding said wafer.

17. The ostomy faceplate of claim 16 in which at least two circumferentially-positioned and individually-removable release strips cover the pressure sensitive adhesive coating of said tape border surrounding said wafer.

18. The ostomy faceplate of claim 1 in which coupling rings are attached to said flexible backing layer for detachably joining said faceplate to an ostomy pouch.

19. The ostomy faceplate of claim 1 in which said removable cover member is flexible, transparent, and substantially planar in an unflexed state.

20. The ostomy faceplate of claim 19 in which said smooth surface of said removable cover member slidably engages said proximal surface of said wafer.

21. The ostomy faceplate of claim 20 in which said cover member includes a finger tab along an outer edge portion thereof for peeling said cover member from said wafer.

22. The ostomy faceplate of claim 20 in which said cover member has an opening concentric with and smaller than said stoma-receiving opening of said wafer.

23. A method for adhering an ostomy faceplate to a wearer, said faceplate including a wafer of soft, finger-moldable, non-memory, hydrocolloid-containing skin barrier material having a generally central opening extending therethrough; said wafer having a proximal bodyside surface and an opposite distal surface; and a releasable cover member having a smooth surface contacting and covering said proximal surface; said distal surface of said wafer having undulations defined by a series of concentric ridges and valleys with said ridges progressively diminishing in thickness, when measured by the distance between the distal and proximal surfaces at each ridge, as said series progresses inwardly towards said opening; comprising the steps of reshaping said opening in a preliminary molding step by slidably displacing the skin barrier material outwardly over the smooth surface of said cover member until said opening approximates the general shape and size of a stoma to be extended therethrough;

removing said cover member from said wafer and positioning said proximal surface of said wafer in sealing engagement with skin surfaces surrounding a stoma;

and then in a second molding step inwardly displacing and molding said barrier material of said wafer into sealing contact with the stoma extending through said wafer opening.

24. The method of claim 23 in which said distal surface of said wafer has an outer zone terminating at the outer periphery of said wafer and a concentric inner zone extending inwardly from said outer zone toward said central opening; and a flexible backing layer over said outer zone; said backing layer extending outwardly beyond said outer periphery of said wafer to define a circumferential border portion about said wafer; said border portion having a proximal surface with a pressure-sensitive adhesive coating covered by at least one release strip; wherein there is the further step of peeling each of said at least one release strip from said adhesive coating of said border portion and adhesively sealing said border portion to the wearer's skin.

* * * * *